United States Patent [19]

Rembaum et al.

[11] 4,123,396
[45] Oct. 31, 1978

[54] IMPREGNATED METAL-POLYMERIC FUNCTIONAL BEADS

[75] Inventors: Alan Rembaum, Altadena; Willi Volksen, Pasadena, both of Calif.

[73] Assignee: California Institute of Technology, Pasadena, Calif.

[21] Appl. No.: 718,103

[22] Filed: Aug. 27, 1976

[51] Int. Cl.² .............................................. C08F 8/42
[52] U.S. Cl. ...................................... 526/24; 427/222; 526/41; 526/47; 526/47.2; 526/47.3; 526/47.4; 526/48.2; 526/48.3; 428/407; 521/55; 526/1; 526/19; 526/23; 528/424
[58] Field of Search .................. 526/48, 47, 48.2, 48.3, 526/24, 47.3, 47.2, 47.4, 41; 260/2 M, 2 T

[56] References Cited

U.S. PATENT DOCUMENTS

| | | | |
|---|---|---|---|
| 3,677,978 | 7/1972 | Dowhinka et al. | 526/48 |
| 3,779,952 | 12/1973 | Leonard | 526/48 |
| 3,824,221 | 7/1974 | Ragg | 526/48 |
| 3,957,741 | 5/1976 | Rembaum et al. | 260/258 |

FOREIGN PATENT DOCUMENTS 1,937,225  1/1970  Fed. Rep. of Germany ............. 526/48

Primary Examiner—William F. Hamrock
Attorney, Agent, or Firm—Marvin E. Jacobs

[57] ABSTRACT

Amine containing polymeric microspheres such as polyvinyl pyridine are complexed with metal salts or acids containing metals such as gold, platinum or iron. After reduction with sodium borohydride, the salt is reduced to finely divided free metal or metal oxides, useful as catalysts. Microspheres containing covalent bonding sites can be used for labeling or separating proteins.

7 Claims, 2 Drawing Figures

IMPREGNATED METAL-POLYMERIC FUNCTIONAL BEADS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to metal-containing polymeric microspheres and to a method of preparing such materials and to the use thereof in catalysis and in labelling, separation and analysis of protein materials.

2. Description of the Prior Art

The isolation and characterization of cell membrane and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and differences in normal and tumor cell surfaces. In previous studies, the localization of antigens and carbohydrate residues on the surface of cells, notably red blood cells and lymphocytes, has been determined by bonding antibodies or lectins to such macromolecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical particles which are bio-compatible, i.e., do not interact non-specifically with cells or other biological components and which contain functional groups to which specific proteins and other bio-chemical molecules can be covalently bonded is disclosed in copending application Ser. No. 434,124, filed Jan. 17, 1974, now U.S. Pat. No. 3,957,741, issued May 18, 1976.

Smaller, more evenly shaped microspheres are disclosed in Ser. No. 634,935, filed Nov. 24, 1975 and microspheres having a density differing from that of cell membranes are disclosed in Ser. No. 634,429, filed Nov. 24, 1975.

The hydroxyl groups can be activated by cyanogen bromide for covalent bonding of proteins and other chemicals containing amino groups to the polymeric latex. Methacrylic acid residues which impart a negative charge onto the particles are likely to prevent non-specific binding to cell surfaces and to provide carboxyl groups to which a variety of bio-chemical molecules can be covalently bonded using the carbodiimide method. Cross-linking of the polymeric matrix is preferable in order to maintain the stability and size of the particles in both aqueous solution and in organic solvents commonly used in the fixation and dehydration of biological specimens for electron or light microscopy.

These polymeric microspheres ranging in diameter from 300 Å to 2000 Å have been successfully utilized as biocompatible immunochemical markers of red cells and lymphocytes in scanning electron and light microscopy. The variable density microspheres have been utilized in separation of labelled cells to which they are attached. The metal containing microspheres can be readily detected by x-ray electron probe methods since the presence of metal causes the microspheres to be electron dense.

Optimum catalysis requires both selectivity and efficiency. A metal containing functional microsphere prepared by polymerization of the microsphere in presence of finely divided metal particles or compounds thereof has been disclosed in Ser. No. 694,151 filed June 9, 1976. However, the distribution of metal within the microspheres is on a random basis, since it is difficult to maintain the particles suspended during polymerization. Impregnation of porous polymeric microspheres on the surfaces of non-porous microspheres with aqueous solutions of metal compounds is not effective since the metal salt dissolves during use in aqueous media.

SUMMARY OF THE INVENTION

Polymeric microspheres containing controlled and uniform distribution of metal atoms are readily custom synthesized according to the invention. Porosity, hydrophilic properties and type and amount of covalent bonding sites are a result of selection of monomer and polymerization conditions of the microsphere substrate.

The metal containing microspheres will find use in a variety of industrial olefin addition processes such as hydrogenation. The catalysts have excellent selectivity due to the control of porosity, metal content and spacing and surface area of the microspheres. Functionally substituted metal-polymeric microspheres have a significant density differential from protein and will find use in separation of labelled cells or cell fragments. The metal containing microspheres are electron dense and can readily be detected by x-ray electron probe methods. Protein labelled with functional polymeric microspheres containing magnetically attractable particles such as iron or magnetite can be separated from non-labelled protein by applying a magnetic field to the cell mixture.

The metal-containing microspheres are hydrolytically stable, biocompatible and have good mechanical strength. The microspheres are of well characterized structure, of outstanding purity and the hydrophilic properties, size, mechanical properties and metal distribution and content can be systematically varied by selection of reactants and conditions.

The metal containing microspheres are synthesized by impregnation of polymeric microspheres containing amine groups, preferably tertiary amine, with an aqueous solution of metal salt or acid to form an ionic or coordination complex between the amine groups and the metal atoms. The metal is found to be firmly attached to the microspheres. Further reaction of the metal-containing microspheres with a reducing agent results in reduction of the metal salt or acid to finely divided, preferably atomic size, black metal particles in a zero or near zero valence state dispersed throughout the microsphere which are in a highly catalytically active form. Reduction of the metal compounds is also desirable for bioassay since metal is a more unreactive state than the precursor metal compound. By utilizing less than the stoichiometric amount of metal with respect to amine, the distance between catalytic centers can be controlled.

These and many other features and attendant advantages of the invention will become apparent as the invention becomes better understood by reference to the following detailed description when considered in conjunction with the accompanying drawings.

DESCRIPTION OF THE PREFERRED EMBODIMENTS

Figure 1:
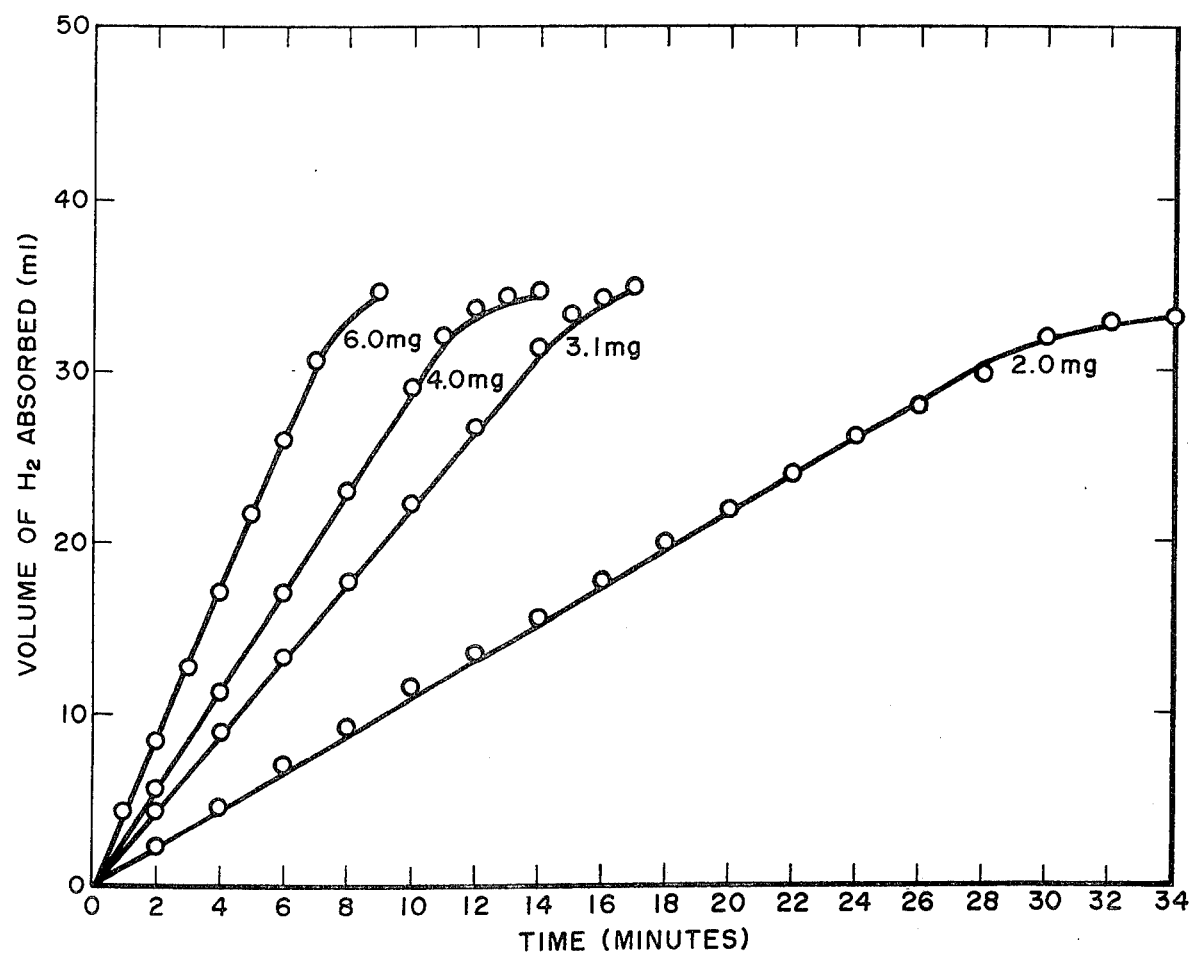
FIG. 1 is a series of curves showing the volume of $H_2$ absorbed in ml as ordinate versus time in minutes as abscissa by the hydrogenation of 1-hexene with poly-4-vinyl pyridine containing 20% by weight of platinum.

The polymeric microsphere is a solid particulate support containing an amine ligand capable of ionic reaction or coordination with a metal containing acid or salt. The amine ligand is preferably a tertiary amine such as $CH_2NMe_2$, $-PhNMe_2$, -pyridyl and the like. The ligand is preferably pendant from the polymer backbone. Representative polymers are cross-linked polystyrene-divinylbenzene substituted with $-CH_2NMe_2$, polyethylene imine, polyvinylbenzimidazole and polyvinylpyridine.

The polymeric support must be insoluble in the polymerization and in the catalytic olefin addition reaction media. The polymeric support may be in the form of particles, sheets, films, strands, hollow fibers or as a coating on a surface. The polymeric substrate is preferably a high area substrate such as a porous particle having a diameter below 100 microns or coated onto a high area inert carrier such as glass particles.

Vinyl pyridine polymers in which the monomer mixture contains at least 20% by weight of vinyl pyridine are preferred due to the ready availability of the pendant pyridyl group for ionic or coordinating reaction with the metal atom. 2-vinyl, 4-vinyl or 2-methyl, 5-vinyl pyridine polymers are suitable. The polymers may be obtained commercially, or can be prepared according to procedures disclosed in application, Ser. No. 671,058, filed Mar. 29, 1976, the disclosure of which is expressly incorporated herein by reference.

The monomer mixture contains at least 20% by weight of vinyl pyridine, preferably at least 50% by weight. The remaining comonomers are soluble in the aqueous medium, compatible, unsaturated compounds capable of addition polymerization with vinyl pyridine. The comonomers preferably contain a hydrophilic group such as carboxyl, amino or hydroxyl.

Mono-unsaturated comonomers are suitably selected from amino, carboxyl or hydroxyl substituted acrylic monomers. Exemplary comonomers are acrylamide (AM), methacrylamide (MAM), acrylic acid, methacrylic acid (MA), dimethylaminomethacrylate or hydroxyl-lower alkyl- or amino-lower-alkyl-acrylates such as those of the formula:

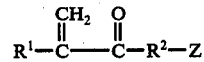

where $R^1$ is hydrogen or lower alkyl of 1-8 carbon atoms, $R^2$ is alkylene of 1-12 carbon atoms, and Z is $-OH$ or $R_3-N-R_4$ where $R^3$ or $R^4$ are individually selected from H, lower alkyl or lower alkoxy of 1-8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of a hydrophilic comonomer.

Water soluble polyunsaturated compounds also provide higher surface area and hydrophilicity and additionally provide cross-linked beads which are more regular in shape and less likely to agglomerate. The polyunsaturated compounds are suitably a liquid diene or triene polyvinyl compound such as ethylene glycol dimethacrylate, trimethylol propane trimethacrylate, N,N-methylene-bis-acrylamide (BAM) or piperazine ethyl methacrylate.

Vinyl pyridines suitable for use in the invention are 2-vinyl pyridine, 4-vinyl pyridine and 2-methyl-5-vinyl pyridine. 2-vinyl pyridine has, in general, been found to produce smaller beads, more resistant to agglomeration even in the absence of cross-linking agents and suspending agents.

The addition of 0.05 to 5% by weight of a stabilizing agent to the aqueous polymerization system before polymerization is found to further reduce agglomeration. The stabilizing agent is suitably an aqueous soluble polymer such as a polyalkylene oxide polyether or nonionic surfactants such as Tween which are polyoxyethylene derivatives of fatty acid partial esters of sorbitol. The polyethers generally have a molecular weight from 10,000 to 10,000,000, preferably 400,000 to 6,000,000 and are polymers of ethylene oxide, propylene oxide or their mixtures. Polyethylene oxides (PEO) are preferred.

The polymerization proceeds without catalyst and with or without stirring with application of high energy radiation capable of generating free radicals to the aqueous system. The radiation source is suitably a cobalt 60 gamma source and doses of 0.5 to 1.0 megarads are sufficient for polymerization. Increased radiation dose up to about 4 megarads or more in absence of cross-linking agent reduces agglomeration and improves the shape of the beads. The reaction is preferably conducted under oxygen excluding condition, generally by applying vacuum to the reaction vessel or by displacing oxygen gas from the system with an inert gas such as nitrogen. After polymerization has proceeded to completion, the polymerization suspension is centrifuged, washed and the trapped water is then removed by azeotropic distillation or freeze drying to yield white, round microspheres at least 80% of which and preferably 90% of which have an average diameter of less than 100 microns, preferably from 100Å to 60 microns and a standard deviation in most cases of no more than 5–40%.

The microspheres can be coalesced into a film by application to a substrate such as a planar surface or particulate surface such as glass beads or polymerized in situ in the presence of the substrate to form a coated substrate. The film consists of a high concentration of microspheres.

The size of the microspheres is dependent on monomer concentration. The vinyl pyridine monomers are soluble in water up to about 3%. Copolymerization with water soluble monomers permits increased water solubility of the monomer mixture up to 6–10% or more. Microspheres produced at 3% vinyl pyridine monomer concentration or less will have a diameter below 3500Å. Solubility of the vinyl pyridine is increased by the addition of a water-miscible solvent therefor such as by replacing up to 50% by weight of the water with a lower alkanol or di or trialkanol such as methanol. The polymerization rate is considerably decreased requiring irradiation of the solution for a longer period. Examples of practice follow.

EXAMPLE 1

4-vinyl pyridine (2.7 g) and bisacrylamide (0.3 g) were irradiated in an aqueous solution containing 0.1% polyethylene oxide (M.W. 600,000) and 3% total monomer with 1.2 megarads from a Co-60 gamma source. The diameter of the microspheres obtained was 2300 Å.

The metal is added to the beads as an aqueous solution of an acid or salt of the metal such as a transition metal compound of metals of Groups IV, VI, VII, or VIII of the Periodic Table having a valence lower than the maximum valence. Typical metals are iron, gold, palladium, platinum, cobalt, nickel, rhodium, manganese, chromium, titanium, ruthenium, tantalum or iridium. Electron dense metals suitable for bioassay are heavy metals having an atomic number above 50, preferably above 75, such as cobalt, platinum, gold, or iron. The metal may be magnetically attractable such as Fe, Ni, Co, or alloys thereof or an inorganic magnetic compound such as a metal oxide. Representative water soluble compounds for use in impregnating the microspheres are chloroplatinic acid ($H_2PtCl_6.6H_2O$), chloroauric acid ($HAuCl_4.3H_2O$), nickel sulfate, nickel chloride, ferrous sulfate ($FeSO_4$), ferrous chloride ($FeCl_2$), cobalt chloride ($CoCl_2.6H_2O$) or the like.

The amount of metal added to the microspheres can be varied from 0.01% by weight to stoichiometric amounts based on amine content of the microsphere and is usually from 5 to 50% by weight thereof. Metal-containing acids react easily in the cold with polyvinyl pyridine forming a strong quaternary bond. Metal salts do not appear to quaternize the pyridyl groups but form a strong ionic bond therewith. Addition of a water-miscible polar or non-polar solvent for the salt such as a lower alkanol containing 1-6 carbon atoms, suitably methanol or ethanol, and/or heating the impregnating solution appears to provide better interaction of the metal salt with the tertiary amino nitrogen.

The metal containing beads are reduced to the free metal or a lower valence metal compound by reaction with a water soluble reducing agent suitably a borohydride or aluminum hydride. Representative materials are cyanoborohydride, lithium aluminum hydride and sodium borohydride. The amount of reducing agent depends on the metal content of the microspheres, the initial valence of the metal and the degree of reduction desired. The reducing agent is usually added in considerable excess with respect to the microspheres, typically at least 1/1 by weight generally 2/1 to 20/1 by weight.

EXAMPLE 2

The microspheres of Example 1 were suspended in a 10 mole % $CoCl_2.6H_2O$ ethanolic solution. An almost quantitative absorption of $Co^{+2}$ was observed.

EXAMPLE 3

Suspension of the microspheres in an ethanolic solution containing 1:1 molar ratio yielded a higher $Co^{+2}$ content.

EXAMPLE 4

The microspheres of Example 1 were suspended in an absolute ethanolic solution of anhydrous $FeCl_3$ at a 1:1 molar ratio. An almost quantitative absorption of $Fe^{+3}$ was observed.

EXAMPLE 5

The PVP microspheres (100 mg) were suspended in 5cc of aqueous methanol (15%) to which was added 400 mg of chloroauric acid. After reaction for one (1) hour at room temperature, the lightly yellow supernatant was separated by centrifugation and the dark yellow microspheres were washed several times with methanol and re-suspended in methanol.

0.2 g of $NaBH_4$ in 70cc of $H_2O$ was added and left overnight. The black microspheres were then passed through a mixed ion-exchange resin bed, centrifuged several times and redispersed in water. Analysis showed the microspheres contained 30% gold.

EXAMPLE 6

100 mg of the PVP microspheres of Example 1 in 5cc of water were treated with varying amounts of 5% solution of chloroplatinic acid, and then separated and reduced according to the procedure of Example 5.

Figure 2:
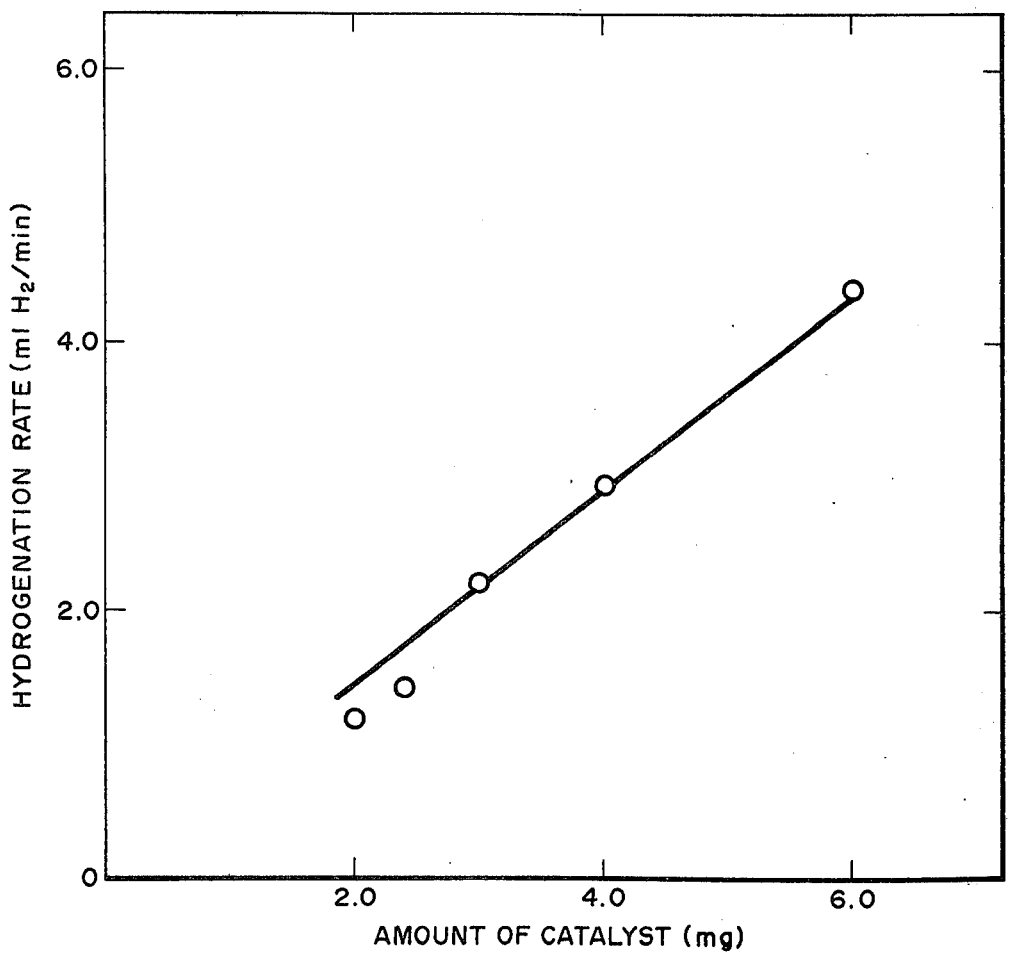
FIG. 2 is a curve showing hydrogenation rate in ml absorbed in $H_2$/min. versus amount of catalyst in mg for the hydrogenation of 1-hexene with the catalytic microspheres of this invention.

The resulting microspheres containing 20% by weight of platinum (6.0, 4.0, 3.1 and 2.0 mg) were utilized to hydrogenate 1-hexene (0.2 ml/10ml methanol) at 24.5° C. The olefin was hydrogenated in 100% yield at room temperature and pressure demonstrating that the finely divided platinum metal associated with the PVP microsphere is a very active, high surface area heterogenous catalyst. This is surprising since pyridine nitrogen usually poisons platinum catalysts. FIGS. 1 and 2 show that the rate of hydrogenation is dependent on the amount of platinum relative to olefin.

EXAMPLE 7

Example 4 was repeated with a PVP copolymer prepared by irradiating an aqueous solution containing 2% total monomer including 60% 4-VP, 30% acrylamide and 10% bisacrylamide. The resulting beads (1000 angstroms in diameter) containing 30% gold are electron dense. These microspheres do not exhibit non-specific binding to living cells, e.g. murine lymphocytes and were found to be capable of binding to antibodies by the cyanogen bromide or carbodiimide reaction. J. Cell Biol. 64 75.

It is to be realized that only preferred embodiments of the invention have been described and that numerous modifications, substitutions and alterations are all permissible without departing from the spirit or scope of the invention as defined in the following claims.

What is claimed is:

1. A metal containing polymeric microsphere composition comprising:

polymeric microspheres having a diameter below 100 microns containing at least 20% by weight of a tertiary amine substituted monomer having the amine ligand pendant from the polymer backbone selected from the group consisting of cross-linked polystyrene-divinylbenzene substituted with —$CH_2NMe_2$, polyethylene imine, polyvinylbenzimidazole and polyvinylpyridine, said ligands being capable of ionic reaction or coordination with Group IV, VI, VII, or VIII metal compounds selected from oxides, salts or acids to form complexes therewith and said microspheres containing; at least 0.1 weight percent of finely divided, free metal associated with the amine ligands formed by reduction of the compound in situ within the microsphere by reaction with a reducing agent selected from the group consisting of borohydrides and aluminum hydrides.

2. A composition according to claim 1 in which the tertiary amino-substituted monomer is vinyl pyridine.

3. A composition according to claim 1 in which the microspheres contain from 5 to 50% by weight of metal.

4. A composition according to claim 1 in which the metal is selected from iron, gold, platinum, palladium, cobalt, nickel, rhodium, manganese, chromium, titanium, ruthenium, tantalum or iridium.

5. A composition according to claim 4 in which the metal is a transition metal which forms a coordination complex with the tertiary amine group.

6. A composition according to claim 4 in which the metal compound is selected from chloroplatinic acid, chloroauric acid, or chlorides, sulfates or carbonyls of the metals.

7. A composition according to claim 1 in which the microsphere monomers include at least 20% by weight of a monomer having at least one covalent bonding group selected from hydroxyl, carboxyl or amine.

* * * * *